United States Patent
Willat et al.

(10) Patent No.: US 8,069,536 B2
(45) Date of Patent: Dec. 6, 2011

(54) CONFORMABLE POD FOR A MANUAL IMPLEMENT

(75) Inventors: Boyd I. Willat, Los Angeles, CA (US);
Adrian Cordova, San Diego, CA (US);
Robert C. Portillo, Carlsbad, CA (US);
Gary D. Delgado, New York, NY (US)

(73) Assignee: Willat Ergonomic Technologies, LLC, Los Angeles, CA (US)

( * ) Notice: Subject to any disclaimer, the term of this patent is extended or adjusted under 35 U.S.C. 154(b) by 1120 days.

(21) Appl. No.: 11/158,900

(22) Filed: Jun. 21, 2005

(65) Prior Publication Data

US 2006/0031994 A1 Feb. 16, 2006

Related U.S. Application Data

(60) Provisional application No. 60/582,263, filed on Jun. 22, 2004.

(51) Int. Cl.
*A47J 45/10* (2006.01)

(52) U.S. Cl. .............. 16/435; 16/110.1; 16/421; 16/430

(58) Field of Classification Search .................... 16/435, 16/422, 431, 421, DIG. 12, DIG. 19; 401/6; 36/43, 153, 181, 15
See application file for complete search history.

(56) References Cited

U.S. PATENT DOCUMENTS

| | | | |
|---|---|---|---|
| 4,404,820 A | 9/1983 | Romaine | |
| 4,867,748 A | 9/1989 | Samuelsen | |
| 4,911,569 A * | 3/1990 | Hashimoto et al. | 401/55 |
| 5,000,599 A * | 3/1991 | McCall et al. | 401/6 |
| 5,098,421 A | 3/1992 | Zook | |
| 5,167,649 A | 12/1992 | Zook | |
| RE35,113 E * | 12/1995 | Grim | 602/14 |
| 5,539,020 A | 7/1996 | Bracken et al. | |

(Continued)

FOREIGN PATENT DOCUMENTS

EP 1419856 A1 5/2004
(Continued)

OTHER PUBLICATIONS

GE Silicones. Gels Material Selector Guide, copyright 2003. p. 2.*
(Continued)

*Primary Examiner* — Victor Batson
*Assistant Examiner* — Emily Morgan
(74) *Attorney, Agent, or Firm* — Lowry Blixseth LLP; Stuart O. Lowry; Scott M. Lowry (57) ABSTRACT

A conformable pod and related method of production are provided, wherein the pod defines a soft structure adapted for deformation in response to minimal pressure applied manually, i.e., by contact with some portion of the body, and for retaining a deformed configuration substantially in the absence of continued application of manual pressure. The pod includes a viscous and tacky gel material encased within a closed chamber defined at least in part by a relatively thin and easily deformed outer skin providing minimal deformation resistance. In a preferred form, the encased gel material is a coagulated or partially coagulated gel such as a silicone-based gel material adapted for deformation in response to minimal applied manual pressure, and for substantially pressureless retention of the as-deformed shape, followed by relatively slow return (at least two seconds or more) to an initial nondeformed shape upon manual release of the pod.

26 Claims, 7 Drawing Sheets

U.S. PATENT DOCUMENTS

| | | |
|---|---|---|
| 5,555,584 A * | 9/1996 | Moore et al. ............... 12/142 N |
| 5,643,187 A | 7/1997 | Naestoft et al. |
| 5,830,237 A | 11/1998 | Kania |
| 5,922,470 A | 7/1999 | Bracken et al. |
| 6,117,119 A | 9/2000 | Gould |
| 6,226,820 B1 * | 5/2001 | Navarro ................. 5/655.5 |
| 6,406,499 B1 | 6/2002 | Kania |
| 6,598,321 B2 | 7/2003 | Crane et al. |
| 6,648,535 B2 * | 11/2003 | Ferrara, Jr. ............... 401/6 |
| 6,725,505 B2 | 4/2004 | Willat |
| 7,004,655 B2 * | 2/2006 | Ferrara ..................... 401/6 |
| 7,159,342 B2 * | 1/2007 | Grisoni et al. ............. 36/180 |
| 2001/0030209 A1 * | 10/2001 | Scott ..................... 223/66 |
| 2001/0045028 A1 * | 11/2001 | Crane et al. ............... 36/44 |
| 2002/0119270 A1 | 8/2002 | Daniel, Jr. |
| 2002/0128580 A1 * | 9/2002 | Carlson et al. ............. 602/54 |
| 2003/0024543 A1 | 2/2003 | Wolf |
| 2003/0051316 A1 * | 3/2003 | Willat ..................... 16/430 |
| 2003/0088946 A1 | 5/2003 | Ferguson et al. |
| 2003/0123917 A1 | 7/2003 | Willat |
| 2004/0126175 A1 * | 7/2004 | Willat ..................... 401/6 |
| 2006/0174450 A1 | 8/2006 | Chen |

FOREIGN PATENT DOCUMENTS

| | | |
|---|---|---|
| WO | 03005858 A | 1/2003 |

OTHER PUBLICATIONS

EIC search report, performed Apr. 12, 2010.*

* cited by examiner

CONFORMABLE POD FOR A MANUAL IMPLEMENT

BACKGROUND OF THE INVENTION

This application claims the benefit of U.S. Provisional Application No. 60/582,263, filed Jun. 22, 2004.

This invention relates generally to improvements in user contact surfaces and related shape-conforming or biomorphic pods and grips for use with manually grasped implements and the like, such as a cooking vessel, hair brush, paint brush, sports racquet or bat, scissors or other hand tool, musical instrument, or virtually any other type of manually grasped device having a handle or related structure for manual grasping or engagement as by means of the hand or fingertips, or alternatively for contact and/or manipulation by a portion of the human body.

More specifically, this invention relates to an improved bio-conforming or biomorphic pod for mounting onto an appropriate implement surface, and a related method of pod production, wherein the conformable pod incorporates a viscous and tacky gel material adapted for custom-fit shape deformation in response to a minimal applied inertia or pressure, and for substantially pressureless retention of the deformed shape until the pod is released by the user. When released, the pod exhibits a memory characteristic for subsequent relatively slow return to an initial nondeformed shape.

Manual implements generally incorporate a handle or related structure having a size and shape for appropriate manual grasping and manipulation of the implement during normal intended use. In one common form, the handle structure comprises an elongated rigid element having one end securely connected to the implement, such as a cooking pot or pan, a hair brush, a tool head, etc. In another common form, the manual implement is normally grasped directly about the body thereof, such as in the case of writing and other marking instruments, baseball and softball bats, etc. Other manual implements are adapted for fingertip manipulation and thereby include one or more keypads for fingertip depression, e.g., keyboards, musical instruments such as a clarinet, saxophone, trumpet and the like. Still other manual implements incorporate handle-like structures of alternative or complex shapes, such as circular structures adapted for finger or fingertip insertion to manipulation the implement, e.g., scissors and shears, and the like. In this regard, a variety of improved grips and the like have been developed in recent years for use with such manual implements, primarily to provide a relatively soft and resilient grip structure for enhanced user comfort and/or improved control of the manual implement during normal use thereof.

In the past, grip structures for relatively large manual implements such as sports equipment, hand tools, cookware, and hair brushes and the like have generally been limited to relatively soft and resilient rubber or rubber-like elastomer sleeves or sleeve-like wraps mounted onto the implement handle. While such grip structures beneficially provide a degree of cushioning for improved user comfort, the relative deformation of such grip structures during normal use is inherently limited. In particular, such cushioned grip structures are generally incapable of significant shape deformation, and thus have generally not provided a high degree of shape deformation needed to assume a customized ergonomical shape conforming closely to the anatomical contours of an individual user's hand and/or fingers. Such customized ergonomic shape is beneficially conducive to substantially optimized user comfort with substantially minimized user fatigue, by providing anatomical pressure relief while enhancing manual dexterity and improving manual control of the related device or implement.

In relatively small manual implements such as writing instruments and the like, cushioned grip structures have been similarly provided in the form of resilient elastomer sleeves and the like. In some designs, an outer resilient sleeve encloses an internal cavity which is filled with a flowable substance such as a deformable putty or relatively viscous liquid adapted to displace and thereby achieve substantial shape deformation when the grip structure is manually grasped. With such deformable grip structures, the outer resilient sleeve can exhibit a relatively high stiffness in comparison with the deformable putty or flowable substance contained within the internal cavity, whereby a significant minimum applied pressure for grip deformation is defined by the structure of the outer sleeve and not by the flowable material contained within said outer sleeve. In this regard, the structural thickness and thus the stiffness of the outer sleeve is often increased with a view toward preventing or minimizing inadvertent sleeve puncture and resultant undesirable escape of the flowable material from the internal cavity. Increased sleeve stiffness is, of course, contrary to a desire to provide a significantly reduced and subtantially minimized pressure threshold for initiating deformation of the deformable grip. Moreover, such grip structures having a flowable material encased within a resilient outer sleeve are difficult to manufacture and assemble.

Exemplary grip structures having a flowable material encased within an outer resilient sleeve or the like are shown and described in U.S. Pat. Nos. 5,000,599 and 6,647,582 and 6,725,505; U.S. Publication Nos. US2003/0123917; and US2003/0051316; and in copending U.S. Ser. No. 09/484,127, filed Jan. 15, 2000 and Ser. No. 10/678,148, filed Oct. 2, 2003; and U.S. Prov. Applns. Nos. 60/473,250, filed May 20, 2003 and 60/477,233, filed Jun. 9, 2003.

There exists, therefore, a need for further improvements in and to deformable pods and grips of the type used with manual implements and the like, particularly wherein a pod or grip structure can be initially deformed to a customized ergonomic shape upon application of an extremely light and substantially minimal pressure, and thereafter retain the deformed shape in substantial conformance with the unique anatomical contours of a specific user, substantially without requiring further or continued application of pressure, followed by relatively slow return upon release of the pod or grip structure substantially to its initial non-deformed shape. The present invention fulfills these needs and provides further related advantages.

SUMMARY OF THE INVENTION

In accordance with the invention, a conformable or biomorphic pod and related method of production are provided, wherein the pod defines a soft structure adapted for mounting onto a user-contacted surface of a manual implement or the like, and for shape deformation in response to minimal pressure applied thereto, i.e., by contact with some portion of the body including but not limited to the fingers, fingertips, and hands, and for retaining a deformed configuration substantially in the absence of continued application of manual pressure. The pod includes a viscous and tacky gel material encased or contained within a closed chamber or cavity defined at least in part by a relatively thin and easily deformed outer skin providing minimal deformation resistance to pod deformation and shape conformance to a substantially customized ergonomic shape conforming with the anatomical contours of the individual user. In a preferred form, the encased gel material is a coagulated or partially coagulated gel such as a silicone-based gel material adapted for deformation in response to minimal applied manual pressure, and for substantially pressureless retention of the as-deformed shape, followed by shape retention for a time delay period following user release (at least about two seconds or more) before relatively slow return (at least about four seconds or more) to an initial nondeformed shape.

A fastener element such as a pressure sensitive adhesive film is carried by the pod for stick-on attachment to a selected surface of a manual implement or the like. In one alternative form, the fastener element may comprise an elongated rim or rib carried by the pod and shaped for assembly as by clamped retention or the like between opposed structures forming the manual implement or the like.

In the preferred form, the gel material comprises a coagulated or partially coagulated or catalized gel or equivalent colloidal material such as a silicone-based gel material adapted for deformation in response to minimal applied pressure. This gel material can be relatively tacky or sticky and thereby adheres to the chamber-defining interior surfaces provided by the overlying pod skin. In one form, the highly deformable pod skin cooperates with a substrate which may comprise a thicker, less deformable material, to define the gel-containing chamber or cavity. The fastener element may be formed on or as part of, or otherwise connected to the substrate.

In use, when the conformable pod is mounted onto a manual implement or the like at a position for user contact during normal implement use, the outer skin is exposed for shape deformation in response to a relatively light or minimal applied manual or tactile pressure or the like. Such shape deformation of the outer skin is accompanied by a corresponding or conforming displacement of the gel material contained within the pod cavity, wherein this gel material tends to retain the deformed shape upon continued contact by the user but without requiring any significant continued application of manual or tactile pressure or the like. Thereafter, following user release of the pod, the gel material exhibits a memory characteristic causing the pod to initially retain the deformed shape following user release for a time delay period of at least about two seconds, and then return relatively slowly over a period of at least about four seconds to its initial nondeformed shape.

The conformable pod may be constructed by initially forming the outer skin as by injection, tumble, compression, or blow molding, or the like. The pod skin, in an inverted orientation, defines an open-sided chamber which is then substantially filled with the gel material, followed by closing and sealing the pod chamber with the substrate.

In one preferred form and method, the skin may incorporate a textured pattern and/or multiple folds in a corrugated configuration at one or more locations or zones for further reducing the requisite tactile force or the like required to deform the pod skin thereby displacing the contained gel material within the enclosed chamber. In this construction, the patterned or folded skin accommodates close control over the timing and/or direction of skin and resultant overall pod displacement. In a modified form, the patterned or folded skin zone or zones may each include a region of reduced or variable skin wall thickness. In each configuration, following user release, the gel material encased by the skin returns slowly to an initial, substantially nondeformed shape.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is an enlarged and fragmented sectional view showing the conformable pod installed onto a user-contacted surface of a manual implement or the like;

FIG. 8 is a fragmented perspective view of a plurality of conformable pods constructed in accordance with the present invention, and connected end-to-end to define an elongated tape or the like adapted for installation onto a manual implement or the like;

FIG. 15 is an exploded perspective view similar to FIG. 14, but showing an alternative mounting arrangement for installing the conformable pod onto a pair of scissors or the like.

DETAILED DESCRIPTION OF THE PREFERRED EMBODIMENTS

As shown in the exemplary drawings, an improved conformable or biomorphic pod referred to generally in FIGS. 1-7 by the reference numeral 10 is provided for use with a manually grasped implement 12 (FIGS. 6-7) or the like. The conformable pod 10 is designed for placement onto a user-contacted surface of the implement 12 where the pod flexibly and resiliently changes shape in response to a relatively small or lightweight applied pressure such as a manual or tactile fingertip pressure or other bodily contact during normal use of the implement 12, so that the pod 10 deformably absorbs energy while conforming geometrically to the unique and customized anatomical contours and particular grasping technique of an individual user. The improved pod 10 of the present invention further is designed to retain the deformed shape upon continuity of manual grasping or bodily contact, but without requiring further application of manual pressure or the like thereto, in combination with memory characteristics for subsequent relatively slow return to an initial nondeformed shape upon manual pressure release. As a result, the conformable pod 10 of the present invention provides anatomical pressure relief resulting in enhanced user comfort and reduced user fatigue otherwise attributable, e.g., to repetitive motion or constant muscular exertion in the act of grasping the pod in the course of implement manipulation. Such anatomical pressure relief is beneficially accompanied by improved user dexterity and control of the implement 12.

The conformable pod 10 of the present invention may be used with a wide range of implements and devices designed or intended for contacting the human skin, particularly such as manually grasped implements including but not limited to items such as a cooking vessel, hair brush, paint brush, scissors, sports racquet or bat, hand tool, musical instrument, or virtually any other type of manually grasped device having a handle or related structure for manual grasping or engagement as by means of the hand or fingertips. In this regard, it will be understood that use herein of the term manual implement will include devices that are grasped, held, manipulated, or otherwise contacted by some portion of a user's body in the course of normal operation and/or use. The conformable pod 10 may be constructed in a wide range of different sizes and shapes, or combination of multiple pods assembled for mounting as a group, onto the handle structure or fingertip keypad structure or other selected user-contacted surface of the related manual implement or the like. In this regard, the pod 10 may be sized and shaped for mounting onto a flat surface, a curvilinear surface, or other geometric surfaces. In addition, the pod 10 may be construction in a cylindrical, sleeve-shaped configuration sized for slide-fit onto an implement handle or the like.

In accordance with a primary aspect of the invention, the conformable pod 10 incorporates a viscous and tacky gel or equivalent colloidal material 14 adapted for resilient deformation when subjected to manual or other bodily pressure. This gel material 14 is contained within a substantially closed chamber 16 defined at least in part by an outer skin 18 formed from a material, and having a thickness selected for minimal deformation resistance to applied lightweight manual or tactile pressure. Accordingly, the easily deformable skin 18 does not provide significant resistance to pod deformation, thereby enabling the encased gel material 14 to deform in response to minimal applied pressure.

Once deformed, the gel material 14 exhibits sufficient shape memory capacity for relatively slow return to its initial nondeformed shape following a time delay of at least about two seconds after release of the applied pressure. Accordingly, after deformation, the gel material retains its deformed shape upon continued user contact, but in a pressureless manner substantially without requiring further input of manual force or pressure to retain the pod 10 in the deformed shape. Following the post-release time delay, the gel material returns slowly over a period of at least about four seconds or more substantially to the initial nondeformed shape. In addition, in the event of inadvertent or accidental puncture of the outer skin 18, the gel material 14 exhibits sufficient material integrity to prevent leakage outflow of the gel material from the pod interior.

Figure 1:
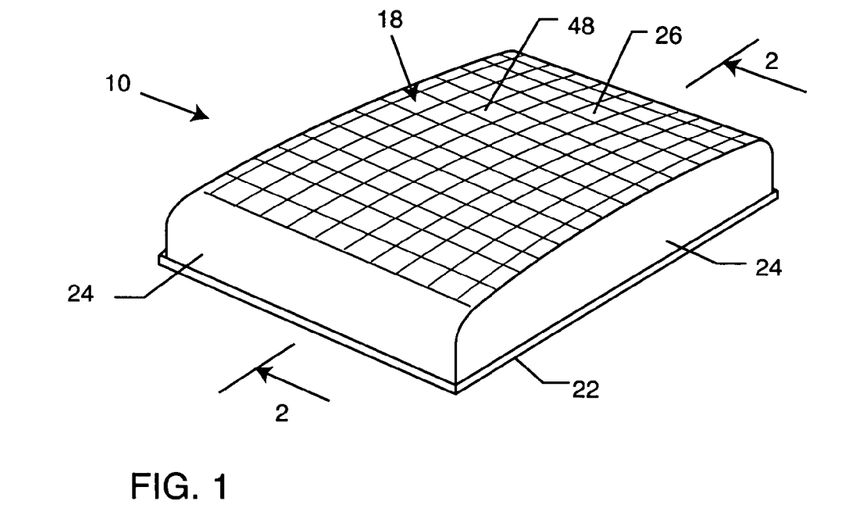
FIG. 1 is a perspective view illustrating a conformable pod for use with a manual implement or the like, constructed in accordance with the present invention.
Figure 2:
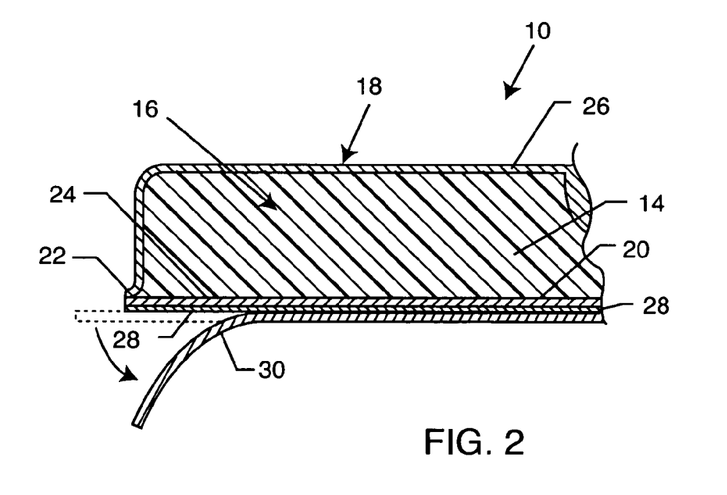
FIG. 2 is an enlarged fragmented longitudinal sectional view taken generally on the line 2-2 of FIG. 1.
Figure 6:
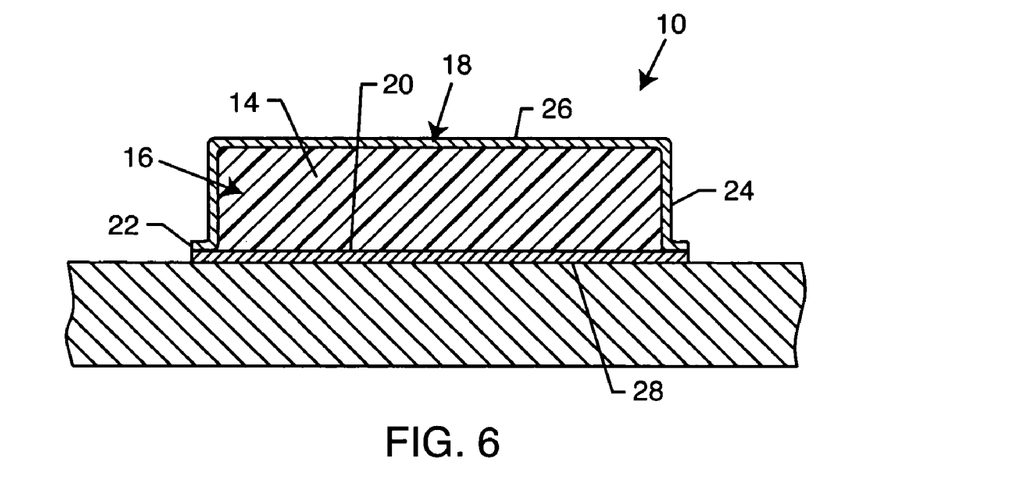
Figure 7:
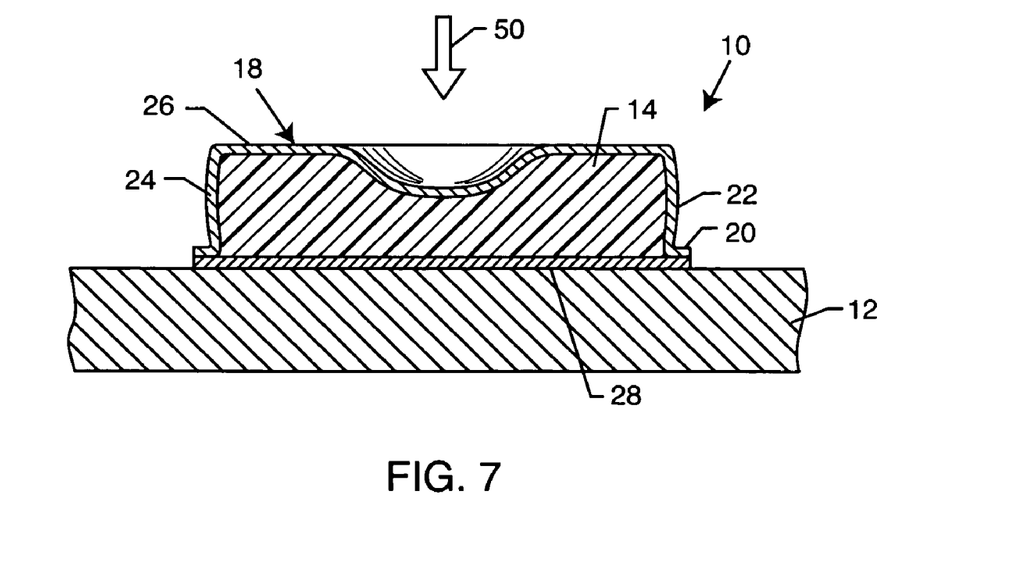
FIG. 7 is an enlarged and fragmented sectional view similar to FIG. 6, but illustrating pod deformation in response to a manual force or the like applied thereto.

As viewed in one preferred form in FIGS. 1 and 2, the conformable pod 10 generally comprises an underlying substrate 20 of generally planar configuration, and which may be relatively thick, stiff, and/or resistant to easy deformation in comparison with the outer skin 18. This substrate 20 is formed in a selected size and shape, such as the illustrative generally rectangular shape. A peripheral margin of the substrate layer 20 is joined as by suitable bonding with a peripheral lower edge 22 of an upstanding perimeter side wall 24 formed as a portion of the overlying skin 18. This upstanding side wall 24 extends upwardly from the substrate 20 and is joined at its upper end to a face wall 26. The assembled skin 18 (defined by the perimeter side wall 24 and the face wall 26) and substrate 20 cooperatively define the enclosed cavity or chamber 16 filled with the deformable gel material 14. A fastener element 28 such as a film of pressure sensitive adhesive of the like is carried at the underside of the substrate 20 for quick and easy affixation of the assembled pod 10 onto a selected implement 12 (FIGS. 6-7). FIG. 2 illustrates a peel-off liner 30 of paper-based material or the like for exposing the fastener film 28 immediately prior to mounting of the conformable pod 10 onto the selected implement.

While the illustrative drawings show the conformable pod 10 to have a generally rectangular shape, persons skilled in the art will understand that numerous alternative pad configurations such as circular, oval, toroidal, cylindrical or sleeve-shaped, etc., may used. Moreover, persons skilled in the art will recognize and appreciate that other types of fastener elements may be employed, such as Velcro-type fastener components, ribs or rims protruding from the substrate 20, and the like.

Figure 3:
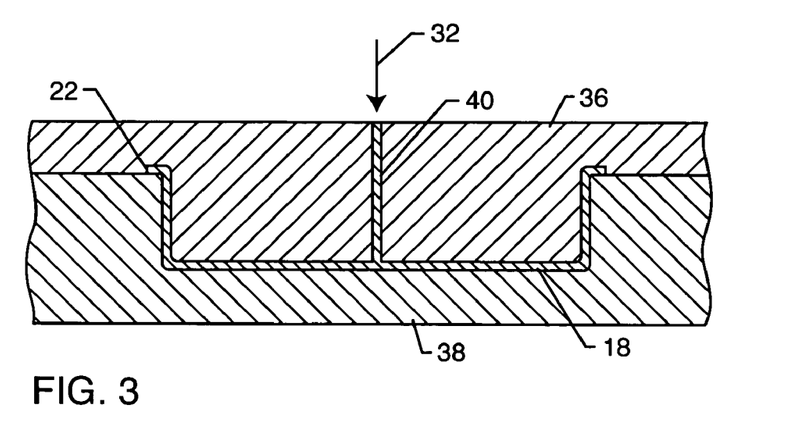
FIG. 3 is an enlarged and fragmented sectional view illustrating an initial process step for constructing the pod of FIGS. 1 and 2.
Figure 4:
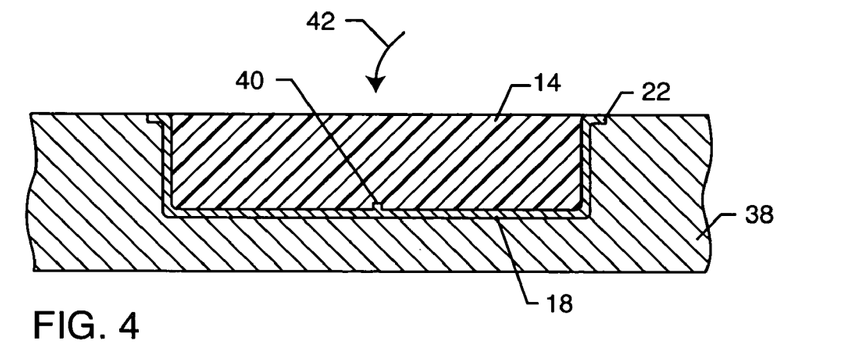
FIG. 4 is an enlarged and fragmented sectional view showing a subsequent process step for constructing the pod.
Figure 5:
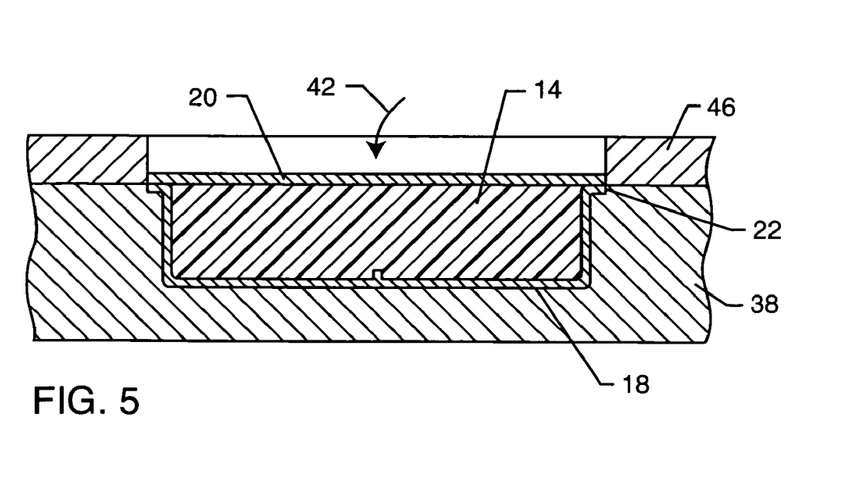
FIG. 5 is a enlarged and fragmented sectional view depicting a further process step for constructing the pod.

FIGS. 3-5 illustrate one preferred process for forming the conformable pod 10 of the present invention. As viewed in FIG. 3, the overlying skin 18 may be formed as by an injection molding process or the like wherein flowable skin-forming material is injected under pressure as illustrated by arrow 32 into a mold cavity 34 defined between a pair of separable upper and lower male and female mold dies 36 and 38. In such molding step, the skin 18 is formed to have a selected overall size and shape, in combination with a selected, relatively thin wall thickness chosen for easy deformation with little and virtually no resistance in response to applied manual pressure. In one preferred form of the invention, the skin material comprises a thermoplastic resin such as a silicone-based or polyurethane elastomer having soft structure (preferred durometer of less than about 40-50 Shore A hardness), and preferably a thin wall thickness of the order of about 0.030 inch. As viewed in FIG. 3, the thus-molded skin 18 may include an integrally molded sprue 40 which is cut therefrom prior to subsequent process steps. Alternative production processes such as tumble, compression, and blow molding will be apparent to persons skilled in the art.

The upper male mold die 36 is then separated from the lower female die 38 having the molded skin 18 supported therein. In this configuration, the molded skin 18 is supported in an inverted orientation for facilitated pour-in reception of the gel material 14, as illustrated by arrow 42 in FIG. 4. The molded skin 18 is substantially filled with the gel material, which preferably comprises a coagulated or partially coagulated or catalized gel such as a highly viscous and tacky silicone or polyurethane gel material wherein the molecules are believed to be attached but not firmly held thereby permitting relative movement in response to applied manual pressure. Importantly, the tacky or sticky character of the gel material causes the gel to adhere or stick intimately with the inboard or underside surface of the inverted molded skin 18, but substantially without fusing or conjoining of the gel material 14 with the skin 18.

Exemplary gel materials include Silgel 612, available from Wacker Chemical Corporation, Adrian, Michigan, and ER 8015 GE TSE3053, both available from GE Silicones, Wilton, Mass. Importantly, such gel materials exhibit a memory characteristic whereby the material deformably responds to relatively lightweight or minimal applied pressure, but thereafter, following a time delay of at least about two seconds after user release, the gel material returns relatively slowly (over a period of at least five seconds or more) to its initial nondeformed shape. The gel material has a preferred penetration range of about 100- 1,000 mm/sec., and preferably a precured viscosity range of about 500 cP (centePoids) to about 1,500 cP.

FIG. 5 shows a subsequent process step wherein the substrate 20 is formed as by pouring (as illustrated by arrow 44) a selected elastomer such as a silicone-based or polyurethane material over the gel material 14, to cooperatively form the enclosed chamber 16 having the gel material sealingly encased therein. For this step, a containment die 46 may be assembled with the lower mold die 38 to retain the thus-poured liquid substrate-forming resin until it cures sufficiently in adhered, substantially sealed engagement with the peripheral edge 22 of the skin 18. Then, the thus-assembled cushioned pad 10 can be removed from the mold die 38 and suitably assembled with the fastener element 28, as previously described (FIG. 2). A shallow textured pattern 48 (FIG. 1) may be defined on the outboard surface of the face wall 26 to facilitate pod removal from the mold die 38, if desired.

FIG. 6 shows the conformable pod 10 of the present invention installed onto a selected manual implement 12, with the pod face wall 26 defined by the thin outer skin 18 presented outwardly for appropriate manual or fingertip contact or the like during use of the implement. FIG. 7 shows deformable response to an applied force such as a manual or tactile force depicted by arrow 50, namely, downward deformation of the thin outer skin 18 with minimal resistance for transferring the applied manual force to the gel material 14 contained within the enclosed chamber. As the gel material 14 deforms, the molecules thereof shift about within the chamber 18, and adhere to the inboard surfaces of the skin and substrate 18 and 20, while absorbing the applied energy. At the same time, the outwardly presented geometry of the skin 18 deformably conforms to the anatomical shape of the person's hand or fingertips or the like in contact with therewith. The result is a highly comfortable, substantially custom-fitted interface between the person's hand or fingertips and the manual implement, thereby reducing friction, irritation, and user fatigue particularly such as fatigue and/or injury associated with and/or attributable to repetitive motion and/or continuity of applied manual force over an extended period of time.

In accordance with one important aspect of the invention, the gel material 14 retains the deformed shape in a substantially pressureless manner, i.e., substantially without requiring the user to exert a deformation force for the purpose of holding and retaining the pod 10 in the desired custom-fitted geometry. Instead, the user can operate and/or manipulate the implement 12 in a secure, stable, and comfortable manner, without requiring continued exertion of additional forces to hold the pod 10 in the desired deformed shape. The gel material 14 maintains the deformed shape for at least a short delay period following release of the applied pressure therefrom. That is, the gel material 14 tends to retain the deformed shape for at least about two seconds or more, following release of the applied pressure, and thereafter returns slowly over a period of about four seconds or more to the initial nondeformed shape.

Figure 8:
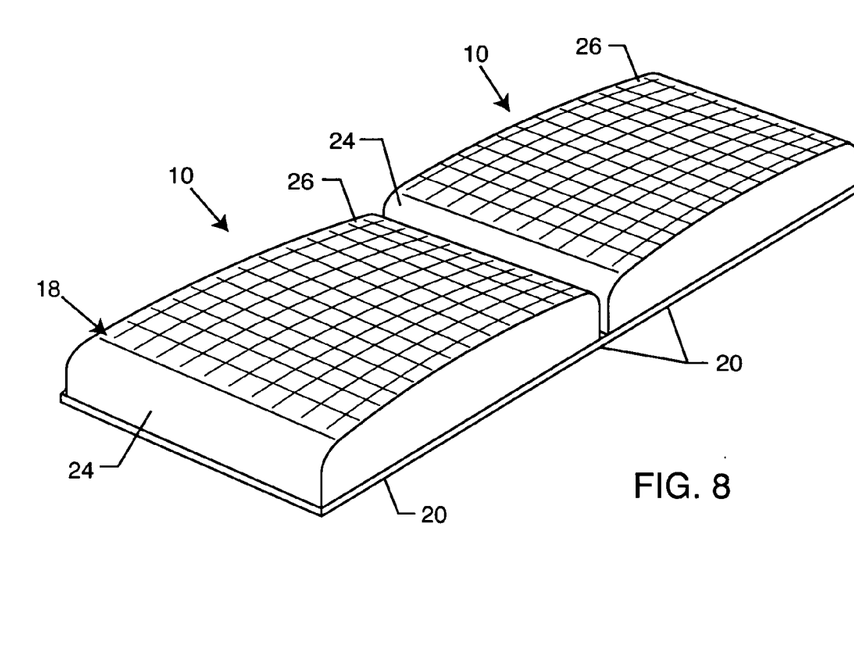

FIG. 8 shows one alternative form of the invention, wherein a plurality of individually formed conformable pods 10 as previously shown and described herein may be assembled as by means of a common substrate 20 to form an enlarged or elongated deformable grip or the like for mounting onto a selected manual implement or the like. Such enlarged or elongated deformable grip may be defined by interconnecting a single row of multiple pods 10 formed end-to-end as shown to defined an elongated tape-like structure adapted for wrapped installation, e.g., about the handle of a manual implement, such as wrapping about the handle of a golf club, baseball or softball bat, or tennis racquet or the like. Alternatively, such tape-like structure may be constructed with multiple rows of interconnected pods 10 to form a wider structure adapted for wrapped or other suitable mounting onto a manual implement or the like.

Figure 9:
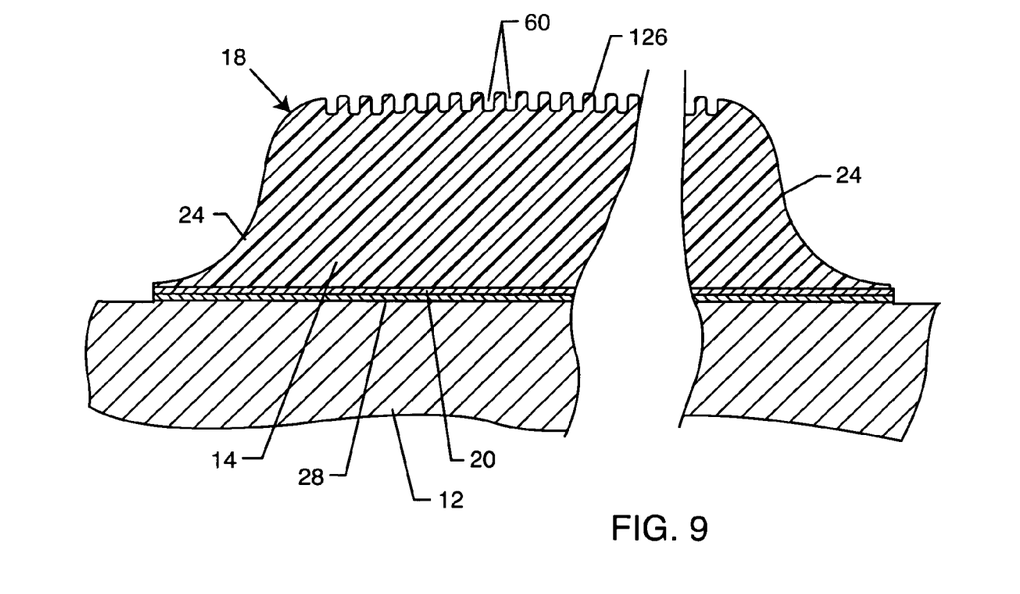
FIG. 9 is an enlarged and fragmented sectional view similar to FIG. 6, but depicting one alternative preferred form of the invention.
Figure 10:
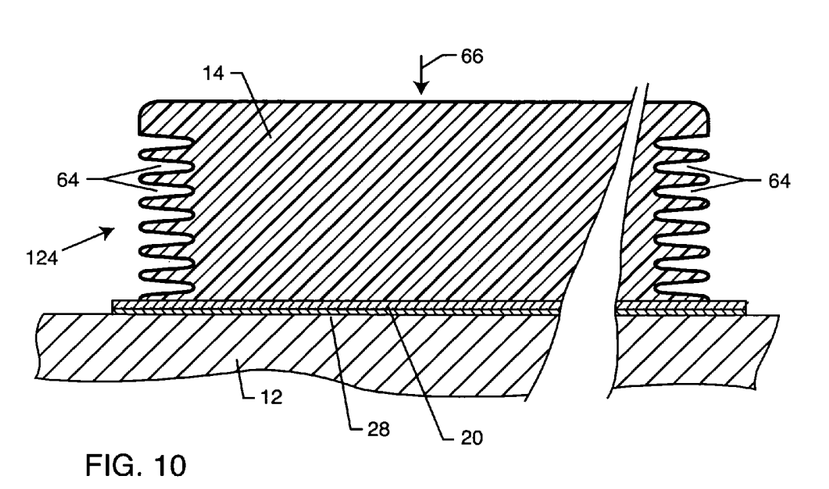
FIG. 10 is an enlarged and fragmented sectional view similar to FIGS. 6 and 9, but showing another alternative preferred form of the invention.
Figure 11:
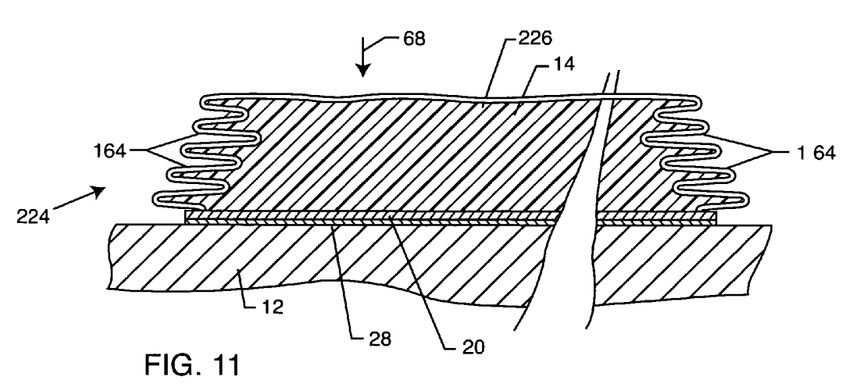
FIG. 11 is an enlarged and fragmented sectional view similar to FIGS. 6, 9 and 10, but illustrating a further alternative preferred form of the invention.

Additional alternative preferred forms of the invention are depicted in FIGS. 9-11, wherein a modified conformable pod is constructed generally as shown and described previously herein, but wherein the overlying skin is modified for further enhanced flexibility, i.e., further reduced resistance to deformation in response to a relatively small or lightweight applied pressure. FIG. 9 shows a modified face wall 126 of the conformable pod to incorporate an array of shallow corrugations 60 designed to decrease resistance to deformation in response to an applied force as illustrated by arrow 62. FIG. 10 shows a modified side wall 124 to incorporate an array of shallow corrugations 64 designed to decrease resistance to deformation in response to an applied manual force as illustrated by arrow 66. FIG. 11 depicts a variation of FIG. 10, wherein corrugations 164 formed in a modified side wall 224 are associated with a variable wall thickness, i.e., the thickness of the side wall 224 is relatively thicker and thus relatively stiffer near the point of attachment with the substrate 20, whereas the thickness of the side wall 224 progressively decreases and thus becomes thinner and more flexible in a direction toward the associated face wall 226. With this construction, the overall resistance of the skin layer to an applied force as illustrated by arrow 68 is reduced.

Figure 12:
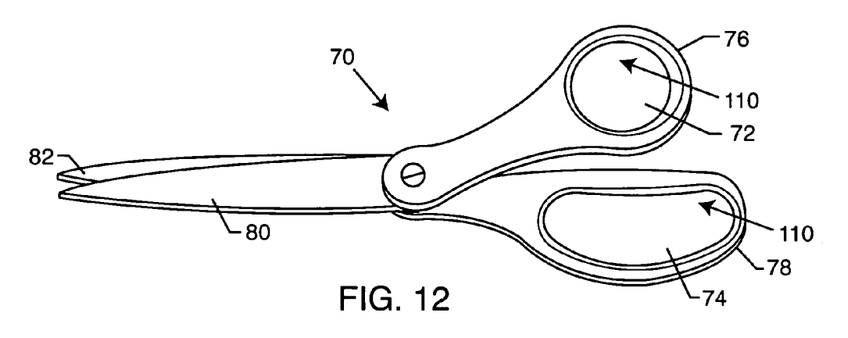
FIG. 12 is a side elevation view of a pair of scissors incorporating a conformable pod constructed in accordance with another alternative preferred form of the invention.
Figure 13:
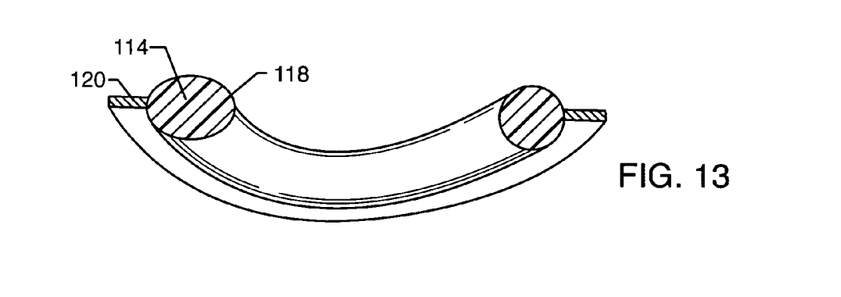
FIG. 13 is an enlarged perspective view, show in partial section, of the conformable pod for use in the scissors depicted in FIG. 12.
Figure 14:
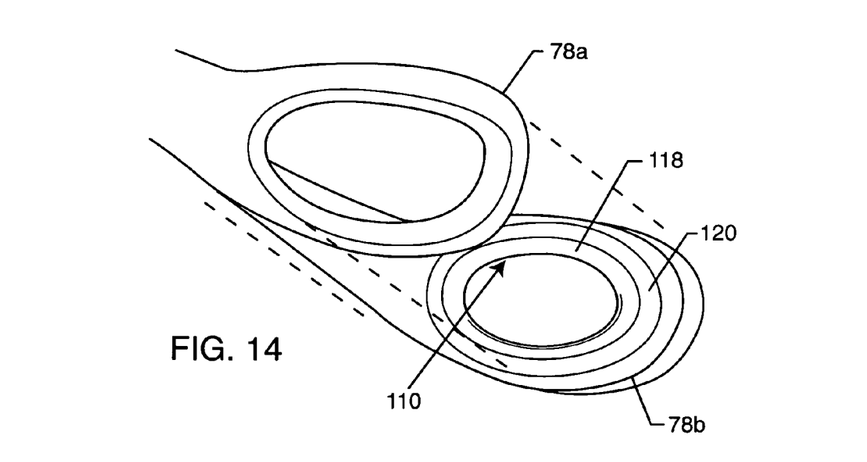
FIG. 14 is an exploded perspective view showing installation of the pod of FIG. 13 onto a pair of scissors.
Figure 15:
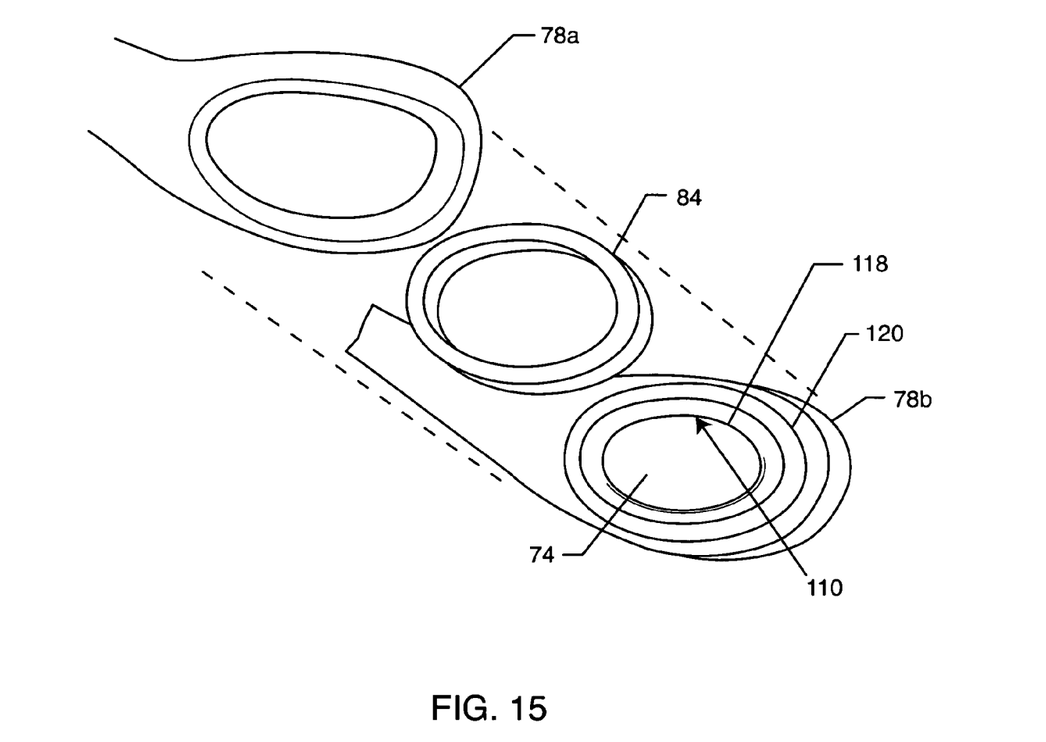

FIGS. 13-15 depict a further alternative preferred form of the invention including one or more modified conformable pods 110, wherein components corresponding structurally and/or functionally with those previously shown and described herein are identified by common reference numerals increased by 100. As shown, the modified pods 110 are constructed in a substantially ring-shaped or closed loop geometry for mounting onto a manual implement or the like such as the illustrative pair of scissors 70. In this regard, FIG. 12 shows a pair of pods 110 mounted on the scissors 70 for lining the inner diameter margins of closed loop openings 72 and 74 provided in a pair of scissors handles 76 and 78 for finger grasping and manipulation of a pair of scissors blades 80 and 82. The conformable pods 110 lining these openings 72, 74 thus provide soft deformable structures for used contact during normal scissors usage.

FIG. 13 shows the conformable pod 110 comprising a closed loop or ring-shaped outer skin 118 having a generally circular cross sectional shape to define an enclosed chamber 116 filled substantially with a flowable material such as a gel or gel-like material 114 preferably exhibiting the deformation and memory characteristics described previously herein with respect to FIGS. 1-11. The outer skin 118 is joined to a substrate rim or rib 120 shown protruding generally radially outwardly from the circumference or outer periphery of the ring-shaped skin 118. This substrate 120 may be constructed from the same material as the skin 118, but with increased thickness, or from an alternative stiffer and/or harder material to provide a sturdy structure adapted for quick and easy mounting of the pod 110 onto the associated scissors handle 76 or 78.

FIG. 14 shows the scissors handle 78 to be constructed from a pair of initially split-apart handle segments 78a and 78b adapted for assembly as by snap-fit and adhesive mounting in face-to-face relation with the protruding substrate rim 120 securely clamped therebetween. FIG. 15 shows a variation in this mounting arrangement wherein a snap ring 84 is additionally provided for seating and locking the substrate rim 120 securely between the interfitting handle segments 78a and 78b. In either assembly technique, the deformable pod 110 defined by the gel material 114 contained within the hollow skin ring 118 is positioned at the inner periphery, or inner diametric edge, of the associated handle opening 72, 74 wherein it is contacted by the user and compliantly deforms as previously described herein to provide the desired customized ergonomic shape. The peripheral rim 120 thus also functions as a fastener element for use in mounting the pod 110 onto the selected implement, it being understood that the ring-shaped pod 110 can be installed onto other types of implements conducive to a closed loop pod geometry.

A variety of further modifications and improvements in and to the improved conformable pod of the present invention will be apparent to those persons skilled in the art. Accordingly, no limitation on the invention is intended by way of the foregoing description and accompanying drawings, except as set forth in the appended claims.

What is claimed is:

1. A conformable pod for a manual implement, comprising:
   a gel material comprising a partially coagulated gel material encased within a closed chamber defined at least in part by a relatively thin and easily deformable outer skin, said partially coagulated gel material adhering to said outer skin, and said partially coagulated gel material having sufficient material integrity to prevent leakage outflow from said chamber upon puncture of said outer skin; and
   means for mounting the pod relative to a manual implement;
   said outer skin and said gel material being deformable to a deformed shape in response to engagement with minimal applied manual pressure, and for substantially pressureless retention of said deformed shape;
   said partially coagulated gel material having a memory for retaining said deformed shape for a predetermined time delay period following release thereof, and for returning relatively slowly following said time delay period substantially to an initial nondeformed shape.

2. The conformable pod of claim 1 wherein said time delay period is at least about two seconds.

3. The conformable pod of claim 2 wherein said gel material further has a memory for returning, following said time delay period, over at least about four seconds substantially to an initial nondeformed shape.

4. The conformable pod of claim 1 wherein said gel material comprises a silicone-based gel material.

5. The conformable pod of claim 1 wherein said gel material has a precured viscosity of about 1,500 centePoise.

6. The conformable pod of claim 1 wherein said outer skin comprises a soft elastomer.

7. The conformable pod of claim 1 wherein said outer skin has a Shore A hardness of less than about 50 durometer.

8. The conformable pod of claim 1 wherein said outer skin has a thickness of about 0.03 inch.

9. The conformable pod of claim 1 wherein said mounting means comprises an adhesive material.

10. The conformable pod of claim 1 wherein said mounting means comprises a rib protruding outwardly from said closed chamber.

11. The conformable pod of claim 1 wherein at least a portion of said outer skin includes a textured region.

12. The conformable pod of claim 1 wherein at least a portion of said outer skin includes a corrugated region.

13. The conformable pod of claim 1 wherein at least a portion of said outer skin includes a region of variable wall thickness.

14. The conformable pod of claim 1 further including a substrate cooperating with said outer skin to define said closed chamber.

15. The conformable pod of claim 14 wherein said mounting means is carried by said substrate.

16. The conformable pod of claim 14 wherein said substrate cooperates with said outer skin to define said closed chamber having a generally closed loop configuration, said mounting means comprises at least one rib protruding outwardly from said closed chamber.

17. The conformable pod of claim 1 further including a substrate cooperating with said outer skin to define a plurality of closed chambers each having said gel material therein.

18. A conformable pod for a manual implement, comprising:
   a relatively thin and easily deformable outer skin;
   a substrate joined to said outer skin to define a substantially closed chamber;
   a gel material comprising a partially coagulated gel material encased within said closed chamber, said partially coagulated gel material adhering to said outer skin, and said partially coagulated gel material having sufficient material integrity to prevent leakage outflow from said chamber upon puncture of said outer skin; and
   means for mounting said substrate relative to a manual implement;
   said outer skin and said gel material being deformable to a deformed shape in response to engagement with minimal applied manual pressure, and for substantially pressureless retention of said deformed shape;
   said partially coagulated gel material having a memory for retaining said deformed shape for a predetermined time delay period following release thereof, and for returning relatively slowly following said time delay period substantially to an initial nondeformed shape.

19. The conformable pod of claim 18 wherein said time delay period is at least about two seconds, and further wherein said gel material returns substantially to the initial nondeformed shape over at least about four seconds following said time delay period.

20. The conformable pod of claim 18 wherein said gel material comprises an at least partially coagulated silicone-based gel material having a precured viscosity of about 1,500 centePoise.

21. The conformable pod of claim 20 wherein said outer skin comprises a soft elastomer having a Shore A hardness of less than about 50 durometer.

22. The conformable pod of claim 20 wherein said outer skin has a thickness of about 0.03 inch.

23. The conformable pod of claim 18 wherein said mounting means comprises an adhesive material carried by said substrate.

24. The conformable pod of claim 18 wherein at least a portion of said outer skin includes a textured region.

25. The conformable pod of claim 18 wherein at least a portion of said outer skin includes a corrugated region.

26. The conformable pod of claim 18 wherein at least a portion of said outer skin includes a region of variable wall thickness.

* * * * *